United States Patent [19]

Ennio et al.

[11] Patent Number: 6,046,172
[45] Date of Patent: Apr. 4, 2000

[54] HYDROLYTICALLY PROCESSED OLIGODEOXYRIBONUCLEOTIDES AND THEIR PHARMACEUTICAL COMPOSITIONS

[75] Inventors: Lanzarotti Ennio, Milan; Mantovani Marisa, Como; Prino Giuseppe, Milan; Porta Roberto, Como; Cedro Armando, Milan; Moltrasio Danilo, Como, all of Italy

[73] Assignee: Crinos Industria Farmacobiologica SPA, Como, Italy

[21] Appl. No.: 07/985,726

[22] Filed: Dec. 4, 1992

[30] Foreign Application Priority Data

Dec. 9, 1991 [IT] Italy ................... MI91A3294

[51] Int. Cl.[7] ............................ A61K 31/70; C07H 21/04
[52] U.S. Cl. .................... 514/44; 536/23.1; 536/25.4; 536/25.41
[58] Field of Search .................. 536/25.4, 25.41

[56] References Cited

U.S. PATENT DOCUMENTS

| | | | |
|---|---|---|---|
| 3,770,720 | 11/1973 | Butti et al. | 536/25.42 |
| 3,899,481 | 8/1975 | Butti et al. | 536/25.41 |
| 4,417,046 | 11/1983 | Hsiung | 536/25.4 |
| 4,605,644 | 8/1986 | Foker | 514/45 |
| 4,623,723 | 11/1986 | Keller et al. | 536/25.4 |
| 4,833,239 | 5/1989 | DeBonville et al. | 536/25.4 |
| 4,985,552 | 1/1991 | Fedeli et al. | 536/25.4 |
| 4,997,932 | 3/1991 | Reardon et al. | 536/254 |
| 5,047,345 | 9/1991 | DeBonville et al. | 435/270 |
| 5,063,162 | 11/1991 | Kiefer | 435/270 |
| 5,126,331 | 6/1992 | Gazzani | 514/44 |

FOREIGN PATENT DOCUMENTS

| | | |
|---|---|---|
| 152148 | 8/1985 | European Pat. Off. . |
| 416677 A1 | 3/1991 | European Pat. Off. . |
| 1245818 | 5/1964 | France . |
| 1408585 | 7/1965 | France . |
| 2131249 | 11/1972 | France . |
| 2651434 | 3/1991 | France . |
| 1142365 | 1/1963 | Germany . |
| 2360110 | 7/1974 | Germany . |
| 60-36493 | 2/1985 | Japan . |
| 0780444 | 4/1985 | U.S.S.R. . |
| 1161511 | 6/1985 | U.S.S.R. . |
| 0808296 | 2/1959 | United Kingdom . |
| 87/06235 | 10/1987 | WIPO . |
| 88/02258 | 4/1988 | WIPO . |

OTHER PUBLICATIONS

New England BioLabs Catalog 1990–1991' Beverly Ma. USA, pp. 62, 63, 73, 83 and 132.

*Primary Examiner*—Douglas W. Robinson
*Assistant Examiner*—L. Eric Crane
*Attorney, Agent, or Firm*—Nikaido, Marmelstein, Murray & Oram LLP

[57] ABSTRACT

The invention discloses new oligodeoxyribonucleotides of animal origin, having a molecular weight comprised between 4000 and 10000 daltons, that can be obtained by fractionation of polydeoxyribonucleotides or otherwise by chemical or enzymatic depolymerization of high molecular weight deoxyribonucleic acids. The new compounds are endowed with a significant anti-ischemic activity.

7 Claims, No Drawings

HYDROLYTICALLY PROCESSED OLIGODEOXYRIBONUCLEOTIDES AND THEIR PHARMACEUTICAL COMPOSITIONS

The invention concerns new oligodeoxyribonucleotides of natural origin, having a molecular weight comprised between 4000 and 10000 daltons and the processes to obtain them.

A further object of this invention is the use of the new compounds as anti-ischemic agents.

It must be preliminary stated here that the above mentioned processes have the general common feature of consisting of a previous depolymerization step of natural high molecular weight deoxyribonucleic acids in aqueous media, followed by precipitation of the oligodeoxyribonucleotides thus obtained by addition of suitable quantities of organic solvents.

The polymers of this invention both for the relevant analytical profile and for the aforementioned pharmacological activity do constitute a particular family amongst all those homologue oligodeoxyribonucleotides with a molecular weight falling inside the hereabove indicated range.

Indeed in that same interval, as it will be shown herebelow, can be found compounds which are different from the substances herein disclosed in the relevant analytical profile, more in detail as to the values of a chemical parameter, and for the much lower anti-ischemic activity.

The chemical parameter hereabove mentioned is the ratio of the sum of moles adenine+thymine/cytosine+guanine, or A+T/C+G, which herebelow reported range (Table I) must therefore be regarded as critical for defining those compounds inside the molecular weight interval 4000–10000 which are endowed with a significant anti-ischemic activity and hence useful from a therapeutic point of wiew.

The state of the art discloses already low molecular weight polymers obtained by depolymerization of natural deoxyribonucleic acids. Anyway, as thoroughly explained in the considerations that will follow, they are not reputed of such relevance as to anticipate the novelty of the new oligodeoxyribonucleotides or otherwise make them a matter of obviousness.

EP-A-416677 discloses cosmetic uses of compositions containing polydeoxy-ribonucleotides of natural origin having a molecular weight comprised between 10000 and 100000 and, for what it is of interest here, a molar ratio purines/pyrimidines (G+A/C+T) encompassed by the corresponding limits set forth for the same parameter in this invention (see Table I).

This disclosure however is not reputed to take away the inventive step of the first object of this invention.

Hence, by example, it would not be at all justified to consider the new polymers as "mere" low molecular weight equivalents of the polydeoxyribonucleotides of this prior art, since the above range of molar ratio G+A/C+T taken as such comprises a very large class of compounds, including both the oligodeoxyribonucleotides endowed of the hereabove referred to pharmacological activity and those that are instead only barely active.

This observation is besides fully confirmed by considering the values and ranges thereof of G+A/C+T set for the compounds of the invention being given in Table I together with that reported at page 10 for preparation P0067.D V which, as shown in following table IV, is instead endowed with a weak anti-ischemic activity The hereabove considerations do afford the unambiguous conclusion that in EP-A-416677 are not given any whatsoever information that could eventually help the man of the art to select or otherwise define the class of polymers herein disclosed. WO 87/06235 teaches polydeoxyribonucleotides of natural origin, which differ from the substances which constitute the first object of this invention for higher values both of the hyperchromicity parameter and optical rotation.

On the issue worth noting is that in the same patent application it is disclosed already that on lowering the molecular weight the hyperchromicity parameter would have decreased. However it must be also acknowledged that the document doesn't instead give any information on how specific rotation would have concomitantly changed.

Further also in WO 87/06235, as said for EP-A-416677, no whatsoever suggestion is being given as to particular values or any thereof interval of the molar ratio A+T/C+G being eventually found of importance for evidencing the disclosed activity of the compounds.

Rather from the reading of both the hereabove referred to documents it appears to be well taken the more general observation that the molar ratio A+T/C+G was therein not even remotely considered for the chemical characterization of such polydeoxyribonucleotides.

Moreover WO 87/06235 provides further, more substantial ground to evidence the non-obviousness of the present invention.

As a matter of facts in the relevant disclosure it is found the statement that low molecular weight polymers of deoxyribonucleic acids having values of the hyperchromicity parameter h lower than 10 should exhibit a dramatic decrease of pharmacologic activity. In addition, it is also affirmed that h is almost zero for oligodeoxyribonucleotides having a molecular weight of 8000.

These propositions lend straightforward to the following conclusions:

a. Oligodeoxyribonucleotides having a value of h less than 10 should have had no therapeutic applications.

b. More in particular, since in the hereabove given reference said impressive decrease of pharmacological activity was put in relation to values of h being lower than 10, the practised artisan would have certainly considered that the lower the value of h the lesser the residual activity, most of all when h=0, which according to WO 87/06235 should correspond, as seen, a molecular weight of such polydeoxyribonucleotides of 8000.

Both these conclusions are indeed manifestly in contrast with the experimental findings of this invention that will be herebelow evidenced.

The relevant physico-chemical and chemical characteristics of the new oligodeoxyribonucleotides are reported in Table I.

The variation ranges therein featured are generally drawn from Table II, except for specific rotation which limits were determined by taking into considerations table II (limits: +34°–+48°) together with examples: specific rotation of preparation P0097.N reported in example 8 (+32.5°) and of preparation P0097.M reported in example 9 (+30.9).

Parameters featured in Table I were determined as follows.

Molecular weight determination for substances of the nature of those of the present invention heavily depends on the method adopted therefor. In the case of HPLC methods the choice of the reference standards is strongy influencing the results. For the present invention the reference standards have been selected taking it into account the similarity of molecular structure or configuration with respect to the oligodeoxyribonucleotides undergoing the analysis.

Molecular weight was determined by HPLC, on a liquid chromatograph equipped with two columns, Biosil$^R$ TSK 300 and Biosil$^R$ TSK 250 (Biorad$^R$) mounted in series, thermostated at 30° C. The solution constituting the mobile phase was obtained by dissolving in distilled water the following substances: sodium chloride 5.844 g, NaH$_2$PO$_4$.H$_2$O 9.24 g, glycine 22.5 g. The volume was afterwards brought to 950 ml, the pH corrected to 6.8 (NaOH 6 N) and then the solution diluted to 1 liter with distilled water.

Flow rate was 0.5 ml/minute, sample volume injected 6 mcl (the abbreviation mcl stands for microliters) and the optical density of the effluent read at 260 nm. Column calibration was effected by using polystyrene sulfonate (sodium salts) standards with a known molecular weight (supplier: Polymers Laboratories Limited). Two solutions, i.e. solution A and B, were used for the calibration. Each of the two contained n. 4 standards at a concentration 0,25%. In solution A the four polystyrene sulfonate standards had the following molecular weights: 1800, 8000, 46000, 200000, whereas in solution B the following: 4600, 18000, 100000, 400000.

TABLE I

Variation limits of the analytical parameters which characterize the oligodeoxyribonucleotides of the invention

| | |
|---|---|
| Molecular weight | 4000–10000 |
| h | <10 |
| A + T/C + G* | 1,100–1,455 |
| A + G/C + T* | 0,800–1,160 |
| Specific rotation | +30°–+48° |

*base molar ratio

Injection of each solution was repeated for three times as a whole.

The sample was injected in the same conditions.

Hyperchromicity parameter h was determined as described in Methods of Enzymology vol. III pages 708–712 (see also page 3 of WO 87/06235).

Optical rotation was determined on an automatic polarimeter at line D of sodium, using a 1% w/v (dry weight basis) sample solution in water, thermostated at 20° C.

Calculation of the base molar ratio A+T/C+G and A+G/C+T required the former determination of the relevant weight percentage of each base in the corresponding oligodeoxyribonucleotide sample. This analysis was made by HPLC, on an ion exchange column after hydrolysis of the sample as described in EP 360882.

The processes by which these substances can be obtained are the following:

Polymer stepwise precipitation from 0.8 M sodium acetate aqueous solutions containing a quantity of 4% w/v of polydeoxyribonucleotide sodium salts having molecular weight comprised in the interval 15000–75000 daltons. The process was carried out at the temperature of 20° C. and precipitation effected by adding to the solution a lower alkyl alcohol, chosen in the group consisting of ethyl, propyl and isopropyl alcohol, according to the steps herebelow reported:
   a. Addition of 0.8 volumes of alcohol to the 0.8 M sodium acetate solution containing 4% w/v of polydeoxyribonucleotides in order to precipitate the great part of the higher molecular weigh polydeoxyribonucleotide fraction.
   b. To the hydroalcoholic solution obtained at preceding point a. containing 0.8 volumes of alcohol, more alcohol was added in order to have as a whole 1 volume of organic phase/volume of starting aqueous phase. The supernatant was then removed and the formed precipitate, which contained the high molecular weight polydeoxyribonucleotide fraction admixed with the polymers of the invention, was recovered and further worked up as described in following step d.
   c. The supernatant of preceding step b was mixed with a further quantity of alcohol so that to have at the end 2 volumes of alcohol/volume of the starting aqueous 0.8 M sodium acetate buffer solution of point a. In such conditions did separate and afterwards recovered the oligodeoxyribonucleotides of the invention.
   d. The precipitate obtained in step b was dissolved in 0.8 M sodium acetate. The high molecular weight polydeoxyribonucleotide fraction was then removed by precipitation by adding 1 volume alcohol/volume of aqueous solution. The precipitate was removed by centrifugation and the left hydroalcoholic solution was admixed with alcohol up to a total quantity of the organic solvent of 2 volumes/volume of the aqueous phase. The precipitate thus formed, constituted of the oligonucleotides according to the invention was recovered.

According to an alternative method to that here above given it could be also effected only one intermediate precipitation by adding to the starting aqueous solution 1 volume of alcohol. In such conditions the supernatant was admixed with one further volume of alcohol, obtaining thus precipitation of the awaited polymers. This process leads anyway to lower yields.

Heat depolymerization of the sodium salts of high molecular weight deoxyribonucleic acids in aqueous buffer acetic acid/sodium acetate 0.5 M pH 4.1. Said process was performed at a temperature varying from 65° C. to 7° C. for a time of at least 6 hours, preferably lower than 10 hours, which time was anyway dependent on the molecular weight of the starting nucleic acid. Depolymerization was followed by monitoring at fixed intervals the polymer molecular weight. The process was carried out until the molecular weight fell within the relevant limits set in Table I.

The deoxyribonucleic acid concentration in said 0.5 M sodium acetate buffer was of 4% w/v or otherwise of about 12% w/v, whereas it appears that with the higher concentration yields are somewhat better (see examples 6–11).

The process consists of the following steps:
   a. Dissolution of high molecular weight deoxyribonucleic acids and subsequent addition of sodium acetate trihydrate+concentrated (80%) acetic acid to give the requested buffer molarity and pH.
   b. Heating the aqueous, viscous solution obtained at the preceding point a at a temperature varying from 65° C. to 75° C. for a time of at least 6 hours.
   c. Lowering at the end of the heat treatment of point b the temperature at 30° C., correcting pH to 7.8–8.0 with 30% NaOH, then heating again at 85° C. for 90 minutes.
   d. Cooling the solution to room temperature, correcting pH to 6.5 with conc. acetic acid and precipitating the oligodeoxyribonucleotides by addition of ethanol in a ratio varying between 1.5 and 2 volumes/volume of aqueous solution.

Depolymerization by deoxyribonuclease of high molecular weight deoxyribonucleic acids and subsequent ultrafiltration step to concentrate the solution.

Enzymolysis was carried out on 1% w/v high molecular weight nucleic acids for a time of 24 hours, in phosphate buffer 0.1 M pH 7.0 in the presence of magnesium chloride 10 mM. At the end the ultrafiltration step was carried out as follows:

a. Ultrafiltration of the solution on a membrane having a cut-off of 10000 daltons until the solution volume was reduced to ⅕ of that starting.
b. Desalting the retentate solution by dialyzing it at constant volume (i.e. adding water to the solution to keep the volume the same as that starting) against 5 volumes as a whole of distilled water.
c. Concentration of the united permeates collected from the preceding steps a and b to ⅕ of the starting volume by ultrafiltration on a 3000 daltons cut-off membrane.
d. Recovery of the solutes dissolved in the retentates of the first (cut-off 10000 daltons, step a) and, respectively, second (cut-off 3000 daltons, step c) ultrafiltration by previous salting the above solutions up to a 0.8 M salt concentration, which salt was preferably sodium acetate, and subsequent precipitation by addition of 1.5 volumes ethanol/volume of aqueous phase.

Alternatively, instead of the above described two ultrafiltration steps, concentration of the solution could be effected according to the following procedure:

a. Ultrafiltration on a 3000 daltons cut-off membrane until the retentate volume is ⅕ of that starting.
b. Desalting of the retentate solution by dialyzing it at constant volume against 5 volumes as a whole of distilled water.
c. Recovery of the solute from the retentate as described at hereabove reported point d.

Said process appears to give about the same yield than the former, with the advantage of a more simple procedure.

In all of the processes hereabove disclosed the compound was then obtained from the precipitate by dehydration, grinding and subsequent drying.

In Table II is reported the analytical profile of those preparations that have been used in the pharmacological assays that will be described herebelow.

The oligodeoxyribonucleotide preparation laboratory code P0067.D V having a molecular weight below 10000, and endowed with a much lower anti-ischemic activity than the polymers of the invention, was obtained according to the fractionation method described in example 15. This preparation showed the following analytical data (dry weight basis) mol. wt. 6600, H 1.4, A+T/G+C 1,494, A+G/T+C 0,914, spec. rot. +37.2. Worth saying is that the same fractionation method used to obtain P0067.D V, when applied to other batches of depolymerized deoxyribonucleic acids gave anyway a product with the same analytical characteristics, i.e. having a high value of the molar ratio A+T/G+C. A suitable demonstration is given in example 16.

In Table III are shown data of fibrinolytic activity of the compounds of the invention, of preparation P0067.D V, and by comparison that of the fibrinolytic agent plasmin, a proteolytic enzyme derived from plasminogen. Worth herein saying that plasmin is as well used in human therapy.

Activity has been expressed as mcg of paranitroanilide (pNA) hydrolyzed from the peptide substrate S-2251 to which pNA is covalently linked.

Said bond is selectively susceptible to the action of fibrinolytic agents.

As a consequence of that the quantity of pNa being released in solution is directly related to the fibrinolytic activity of the assayed compound.

Fibrinolytic activity has been tested in vitro, using the tripeptide S-2251 (H-D-valil-L-leucil-L-lysine paranitroanilide dihydrochloride Kabi—Milan) as essentially described by J. H. Verheijen et Alii in "A simple sensitive spectrophotometric assay for extrinsic (tissue-type) plasminogen activator applicable to measurements in plasma" Thromb. Haemostas. 48 (3) 266–269 1982.

Plasma euglobulin fraction was prepared by collecting blood (8 ml) from the marginal vein of rabbit's ear by means of a syringe containing already 2 ml of sodium tribasic citrate 3.8% w/v solution. Plasma obtained by centrifugation was then divided into aliquots of 0.5 ml, and each aliquot added of 1 ml of the solution of oligonucleotide in such a manner as to have at the end the following two sample concentrations: 200 and 800 mcg/ml of plasma (mcg stands for micrograms). To the solutions were added 0.1 ml of urokinase (50 U./ml) aqueous solution to convert plasminogen into plasmin. Acetic acid was added in order to bring the pH to 5.4 and then the solution volume was adjusted to 8.5 ml with cold distilled water at +4° C. in order to obtain euglobulin precipitation. The step was completed by transferring the test tubes in a refrigerator (+40° C.) for 2 hours. Centrifuging was then effected for 10 minutes and the supernatant discarded. The residue was taken up with 0.3 ml of tris hydrochloride solution buffer at pH 7.4, bringing about a suspension. To 0.3 ml of the suspension was added 0.4 ml of buffer tris hydrochloride and then incubated for further 10 minutes at 37° C. It was then added the tripeptide S-2251 (8.25 mg of the substance in 5 ml of distilled water) and it was incubated for further 5 minutes at the same temperature. Enzymolysis was blocked by adding 0.1 ml of 1% acetic acid and 0.6 ml of 0.15 M NaCl. The quantity of chromogen released in the test solutions was determined by spectrophotometry. The reference standard curve was made with bacterial plasmin U.S. (Biosintex) assayed in the same test at the following doses: 40, 80, 160 320 mcg. The experiments were repeated 6 times altogether, each time assaying the sample and the four above reported plasmin concentrations.

Results are reported in Table III.

TABLE II

Physico-chemical and chemical characteristics of the oligonucleotide preparations that have been used in the pharmacological tests. In the heading of each column is reported the laboratory code.

|  | P0085.C | P0085.D IV | P0085.M II | P0130.A | P0130.C | P0102.A | P0102.B |
|---|---|---|---|---|---|---|---|
| Molecular weight | 8500 | 6400 | 9500 | 8000 | 9400 | 8000 | 4500 |
| h | 9.4 | 3.9 | 9.0 | 3.5 | 5.8 | 9.7 | 3.9 |
| A + T/G + C * | 1.298 | 1.446 | 1.305 | 1.263 | 1.230 | 1.120 | 1.110 |
| A + G/T + C * | 0.908 | 0.849 | 0.917 | 0.806 | 0.854 | 1.150 | 1.096 |
| specific rotation | +47.3° | +38.6° | +46.2° | +34.8° | +36.2° | +46.8° | +47.3° |

* Molar ratio

A general feature that can be drawn from the data of Table III is that oligodeoxyribonucleotides having a molecular weight lower than 10000 show a weak, or otherwise null fibrinolytic activity.

This moreover was to be expected already in wiew of the teaching of WO 87/06235. Anti-ischemic activity was performed ex-vivo on the isolated and perfused rabbit heart, basically as described by P. D. Henry in the paper "Myocardial contracture and accumulation of mitochondrial calcium in ischemia rabbit heart" Am. J. physiol. 233, 1977.

Test compounds were perfused starting from 40 minutes before the ischemic event at the concentration of 400 mcg/ml and flow rate of 20 ml/minute.

During the ischemic phase (40 minutes) flow rate was reduced to 0.2 ml/min. At the end of this phase the starting flow rate was restored and maintained for further 20 minutes. The experiment was repeated for 6 times altogether. During the ischemic phase and the subsequent reperfusion the left ventricular telediastolic pressure of the treated hearts was determined and values referred to the untreated (control group).

In Table IV are reported the anti-ischemic activities of the compounds under examination determined, as shown in said Table, both during ischemic and following reperfusion phase. From said Table it is evident that the

TABLE III

In-vitro fibrinolytic activity of the new oligonucleotides evaluated on the chromogenic substrate tripeptide S-2251

| Compound | mcg of paranitroaniline released from substrate S-2251 in 5 minutes Compound concentration | |
|---|---|---|
| | 200 mcg/ml | 800 mcg/ml |
| P0085.C | 0.25 ± 0.16 | 0.89 ± 0.38 |
| P0085.D IV | 0.18 ± 0.09 | 0.03 ± 0.03 |
| P0085.M II | 0 | 2.49 ± 0.70 |
| P0102.A | 1.27 ± 0.52 | 2.63 ± 0.61 |
| P0102.B | 0.87 ± 0.57 | 0.56 ± 0.27 |
| P0067.D V | 0 | not determined |
| Plasmin | 6.70 * | 27.01 * |

* values extrapolated from the equation of plasmin regression line y = −0.26 + 0.0341x ( r = 1 )

TABLE IV

Ex-vivo anti-ischemic activity of the new oligonucleotides

| | % Inhibition vs ischemic damage Experimentally induced ischemia | |
|---|---|---|
| Compound | Ischemic phase | Reperfusion phase |
| P0085.C | 67 | 80 |
| P0085.D IV | 66 | 77 |
| P0085.M II | 68 | 79 |
| P0102.A | 61 | 69 |
| P0102.B | 42 | 60 |
| P0130.A | 63 | 74 |
| P0130.C | 57 | 66 |
| P0067.D V | 23 | 37 | oligodeoxyribonucleotides complying with the analytical profile set in Table I show a significant anti-ischemic activity. On the contrary preparation P0067.D V, which has a base molar ratio A+T/G+C (1,494) outside the limits 1.100–1.455 set in Table I, evidences a much lower activity.

The meanings of these data can be better understood taking into consideration that when in said experimental model cardiac ischemia is brought about on reducing flow of the perfusing liquid, heart is being hit by a damage which is evidenced functionally by ventricular contracture. In the following reperfusion phase, on re-establishing the starting flow rate conditions, it is being brought about an even worst impairment since together with increase of diastolic pressure, already observed in the preceding phase, there is a concurrent onset of cardiac arrhythmias.

From the data of Table IV it is drawn the conclusion that in the final reperfusion phase the oligonucleotides of the invention afford a substantial protection from experimentally induced ischemia, thus substantially maintaining the regular contractile activity of heart with reduction of the diastolic resistance thereof.

As a consequence of what it has been hereabove demonstrated, it is concluded that the new compounds can be usefully exploited in the therapy of cardiac ischemia.

Further objects of the invention are the dosage forms containing as the active principle the new substances. Said formulations can be intended both for parenteral and oral administration.

Parenteral compositions can be in the form of sterile and apyrogenetic solutions in sealed ampoules, or otherwise liophylizates contained in sealed bottles to be dissolved extemporarily in aqueous sterile solvents.

As aqueous solvents can be used isotonic solutions made with conventional buffers (citrates, phosphates and the like) together with known preservatives.

Oral formulations can be available in the form of tablets, coated tablets, gelatin capsules, granules.

Said dosage forms can be prepared according to known techniques.

For instance oral dosage forms can be prepared by direct compression of powders or granulates and may contain binders, lubricants and known disaggregating agents.

Dosage forms for parenteral administration may contain from 40 to 200 mg/ml of the active principle, preferably from 80 to 160 mg/ml (for the liophylizates the preceding figures refer to the final concentration of the substance in the sterile solvent), those for oral administration between 200 and 1500 mg for unit dose.

EXAMPLE 1

Isolation of the oligonucleotides according to the present invention (preparations P0085.C and P0085.M II) by fractional precipitation from an aqueous solution of defibrotide in the presence of sodium acetate by addition of ethanol.

420 g of defibrotide (lot 82) were dissolved in 10.5 l (final concentration 4% w/v) and added of 1155 g of sodium acetate trihydrate (0.8 M). The solution was thermostated at 20° C. 0.8 volumes of ethanol 95% were then added. The supernatant was recovered by centrifugation (the precipitate constituted of high molecular weight polydeoxyribonucleotides was discarded) and added of 0.2 volumes of ethanol (total volume organic phase/aqueous phase=1). Centrifuging was again effected. The precipitate was recovered, dehydrated, dried and ground. As a whole were recovered 97.6 g (preparation P0085.B, consisting of a mixture of the oligodeoxyribonucleotides of the invention together with polydeoxyribonucleotides).

To the supernatant more ethanol was added in order to have 2 volumes of the organic solvent/volume of aqueous phase. 40.5 g of a solid were thus recovered (preparation P0085.C).

97.6 g of P0085.B were dissolved in 2.45 l of distilled water and added of 269.5 g of sodium acetate trihydrate. The solution was thermostatted at 20° C. 1 volume of ethanol was added and the suspension thus obtained centrifuged. To the supernatant more ethanol was added in order to have a final ratio of 2 between the overall quantity of ethanol and that of the aqueous solution. 31.2 g (preparation P0085.M.II) were then recovered.

Total recovery of oligodeoxyribonucleotides, i.e. P0085.C+P0085.M II, was of 71.7 g (17.1%).

EXAMPLE 2

Isolation of oligonucleotides (preparation P0085.D IV) by fractional precipitation with ethanol in the presence of sodium acetate from an aqueous solution containing defibrotide.

20 g of a defibrotide preparation having molecular weight 17000 daltons were dissolved in 500 ml of distilled water. 55 g of sodium acetate trihydrate were added and the resulting clear solution thermostatted at 20° C. 500 ml (1 volume) of ethanol were then added and the precipitate collected by centrifuging at 3000 rpm for 5 minutes. To the supernatant were added 500 ml (i.e. 2 volumes as a whole in the confront to that of the aqueous phase) of ethanol. The solid was recovered, dehydrated, ground and dried in an oven. 2.10 g were thus obtained. Yield: 10.5%.

EXAMPLE 3

Isolation of oligonucleotides (preparation P0085.D V) by fractional precipitation with ethanol in the presence of sodium acetate from an aqueous solution of a polydeoxyribonucleotide.

20 g of the sodium salt of a polydeoxyribonucleotide having a molecular weight of 43000 daltons were dissolved in 500 ml of distilled water. It was then followed the procedure disclosed in preceding example 2. 1.46 g were obtained at the end (yield 7.3%). The substance thus isolated had the following analytical characteristics (data on a dry weight basis,): mol. wt. 6700, h 3.4, A+T/G+C 1.375, G+A/T+C 00.825 spec. rot. +43.4.

EXAMPLE 4

Isolation of oligonucleotides (preparation P0085.D VI) with the procedure of example 2.

20 g of defibrotide lot n. 157, having molecular weight 26200, were processed according to said example. 1.54 g (yield 7.7%) were recovered at the end. The analytical data (data on a dry weight basis) were the following: mol. wt. 5900, h 5.7, A+T/G+C 1.343, A+G/T+C 0.835, spec. rot. +41.6.

EXAMPLE 5

Isolation of oligonucleotides (preparation P0085.D VII) by fractional precipitation with ethanol in the presence of sodium acetate from an aqueous solution of a polydeoxyribonucleotide.

20 g of the sodium salt of a polydeoxyribonucleotide having a molecular weight of 75000 daltons were dissolved in 500 ml of distilled water. It was then followed the procedure given in preceding example 2. Were obtained g. 0.78 (3.9%) of a compound which had the following characteristics (data on a dry weight basis) mol. wt. 6100, h 7.1, A+T/G+C 1.415, G+A/C+T 0.860, spec. rot. +43.6.

EXAMPLE 6

Preparations of the oligonucleotides of the invention by chemical depolymerization in aqueous buffer sodium acetate/acetic acid (preparation PO130.A). 800 g of high molecular weight deoxyribonucleic acid (mol. wt. higher than 700.000) were dissolved in 5280 ml $H_2O$ with moderate heating. 426.4 g of sodium acetate trihydrate were added, followed by 1.016 ml of acetic acid 80% (conc. acetic acid) were then further added to correct pH to 4.1 and then the viscous solution (final polymer concentration 12.7% w/v; sodium acetate molarity 0.5 M) was heated at 75° C. for 6 h. After this time the temperature was lowered at 30° C., the pH corrected at 7.8–8.0 with 30% NaOH and the solution further heated at 85° C. for 90 minutes. After cooling, pH was brought to 6.5 with 80% $CH_3COOH$. Precipitation was then effected by addition of 1.5 volumes ethanol/volume aqueous phase. The solid recovered was washed, grounded, and dried.

Obtained 745 g (yield 93,1%)

EXAMPLE 7

Preparations of the oligonucleotides of the invention by chemical depolymerization in aqueous buffer sodium acetate/acetic acid (preparation PO.130.C). 800 g of high molecular weight deoxyribonucleic acid were treated as in example 6.

At the end were obtained 765 g of product (yield 95.6%)

EXAMPLE 8

Preparation of the new substances by depolymerization in a buffer solution acetic acid/sodium acetate (preparation P0097.N).

50 g of high molecular weight nucleic acids were dissolved at a temperature of 70° C. in 1 l of water. 80 g of $CH_3COONa.3H_2O$ and 190 ml of $CH_3COOH$ 80% (final pH 4.1) were then added (polymer concentration: 4% w/v; sodium acetate molarity: 0.5 M). The resulting solution was heated at 70° C. for 24 hours. Cooling was then effected and the temperature lowered at 30° C. and afterwards followed the procedure described in preceding example 6. 33.5 g of product (yield 67%) were obtained. Analysis (on a dry weight basis): mol. wt. 8100, h 5.3, A+T/G+C 1.037, A+G/T+C 0.865, spec. rot. +32.5.

EXAMPLE 9

Preparation of the new substances by depolymerization in aqueous buffer acetic acid/sodium acetate (preparation P0097.M)

50 g of high molecular weight nucleic acids were processed as reported in example 8, whereas the depolymerization time was instead reduced at 16 h and the precipitation was made by adding 2 volumes of ethanol. 35.5 g (yield 71%) were recovered. Analysis (on a dry weight basis): mol. wt. 6200, h 1.0, A+T/G+C 1.167, A+G/T+C 0.830, spec. rot. +30.9.

EXAMPLE 10

Preparation of the oligonucleotides by depolymerization in aqueous buffer acetic acid/sodium acetate (preparation P0123.B).

100 g of high molecular weight nucleic acids were dissolved in 660 ml $H_2O$ Dissolution was then effected with a moderate heating. 53.5 g of $CH_3COONa.3H_2O$ and 127 ml 80% acetic acid were in the order added.

Final pH was 4.1 and polymer concentration 12.7% w/v (salt molarity 0.5 M). The resulting solution was then heated at 65° C. for 16 hours and then treated as described in example 6. Obtained 78,6 g of product. Analysis (on a dry weight basis) mol. wt. 9400, h 6.4, A+T/G+C 1.174, A+G/T+C 0.941, spec. rot. +38,9.

EXAMPLE 11

Preparation of the oligonucleotides by depolymerization in aqueous buffer acetic acid/sodium acetate (preparation P0123.H).

100 g of high molecular weight deoxyribonucleic acids were processed as described sub example 10. Depolymerization time was fixed at 22 h. Obtained 85.9 g Analysis (on a dry weight basis): mol. wt. 7000, h 1.9, A+T/G+C 1.305, A+G/T+C 0.875, spec. rot. +35,4.

EXAMPLE 12

Preparation of the oligonucleotides according to the invention by enzymatic depolymerization of high molecular weight deoxyribonucleic acids by means of deoxyribonuclease (preparations P0102.A and P0102.B).

10 g of the sodium salt of high molecular weight nucleic acids were dissolved in 1 l of 0.1 M phosphate buffer pH 7 and $MgCl_2$ 10 mM.

To the final viscous, opalescent solution were added 3.67 g of raw deoxyribonuclease. Enzymolysis was carried out at 37° C. for 24 hours. At the end the solution volume was reduced to 1/5 of that starting by ultrafiltration on a membrane having a cut-off of 10.000 daltons. 0, 81 of permeate was collected.

The concentrate (retentate) was desalted by dialyzing it at constant volume against 1. 1 of water and precipitated by adding 22 g sodium acetate trihydrate (0.8 M) followed by 1.5 volumes of ethanol. 4.88 g (yield 49%) were obtained (preparation P0102.A).

The permeates from the above reported ultrafiltration and desalting steps were united and concentrated to 1/5 of the starting volume by ultrafiltration on a 3000 daltons cut-off membrane.

The solution was then desalted by dialyzing it at constant volume against 5 volumes of water and liophylized. 24.7 g (yield 25%) were obtained (preparation P0102.B)

EXAMPLE 13

Preparation of the oligonucleotides by enzymatic depolymerization with deoxyribonuclease of high molecular weight deoxyribonucleic acids (preparations. 0186/91220A and 0186/91220B)

5.5 g of the sodium salt of high molecular weight deoxyribonucleic acids were dissolved in 1 l of 0.1 M pH 7 phosphate buffer containing 10 mM $MgCl_2$. It was then followed the procedure of preceding example 12.

From the retentate solution were obtained g 1.14 (20.7%) of compound (0186/91220.A) having the following analytical characteristics (data on a dry weight basis): mol. wt. 5000, h 5.4, A+T/C+G 1.266, A+G/T+C 1.106 spec. rot. +39.1. From the permeate solution were obtained 2.20 g (40%) of compound (0186/91220.B) having the following characteristics (data on a dry weight basis): mol. wt. 4600, h 0.8, A+T/G+C 1.168, A+G/T+C 1.087, spec. rot. +37.4.

EXAMPLE 14

Preparation of the oligonucleotides by enzymatic depolymerization of high molecular weight deoxyribonucleic acids (preparation 0186/91217).

11 g of high molecular weight nucleic acids were dissolved in 1.1 l of the buffer referred to in the preceding example. Digestion was performed by using deoxyribonuclease according to the procedure of example 12. The solution volume was then reduced to 1/5 of that starting by ultrafiltration on a 3000 daltons cut-off membrane. After desalting the retentate by dialyzing it at constant volume against 5 volumes of distilled water the solution was salted an precipitated as described in example 12 for preparation P0102.A. At the end were obtained 8.25 g (75%) of a product having the following characteristics (data are given on a dry weight basis): mol. wt. 5600, h 5.8, A+T/G+C 1.140, A+G/C+T 1.010, spec. rot. +41.5.

EXAMPLE 15

Method used to obtain P0067.D V.

1.68 of the mother liquors from the precipitation of polydeoxyribonucleotides obtained by depolymerization of high molecular weight deoxyribonucleic acid (preparation of defibrotide lot n. 73) according to the method disclosed in WO/87/06235 and still containing a theoretical quantity of 1250 g of deoxyribonucleic acids, 1 part of acetate buffer aqueous solution and 1.5 parts of ethanol, were added of further 13.6 l (0.5 parts) of the same organic solvent the product thus precipitated weighed 36.4 g.

EXAMPLE 16

Isolation of preparation P0067.D IV.

1. 68 of the mother liquors from precipitation of polydeoxyribonucleotides obtained by depolymerization of high molecular weight deoxyribonucleic acids (preparation of defibrotide lot n. 72) according to the method disclosed in WO 87/06235 and still containing a theoretical quantity of 1250 g of deoxyribonucleic acids, were treated as in example 15. Were obtained 34.8 g of preparation P0067.D IV having the following analytical characteristics (data on a dry weight basis): mol. wt. 6100, h 0, A+T/C+G 1.508, A+C/T+C 0.917, spec. rot. +35,9.

EXAMPLE 17

Pharmaceutical composition for parenteral use.

| Sealed ampoules | |
| --- | --- |
| oligodeoxyribonucleotides | 250 mg |
| trisodium citrate dihydrate | 25 mg |
| methyl p.hydroxybenzoate | 3.13 mg |
| propyl p.hydroxybenzoate | 0.62 mg |
| distilled water | 2.5 ml |

EXAMPLE 18

Pharmaceutical composition for oral use.

| Hard gelatin capsules | |
| --- | --- |
| Oligodeoxyribonucleotides | 350 mg |
| lactose | 56,75 mg |
| colloidal silicon dioxide | 0,7 mg |
| magnesium stearate | 3 mg |

We claim:

1. An oligodeoxyribonucleotide having the following analytical parameters: mol. wt. 4000–10000 Dalton, h<10, A+T/C+G 1.100–1.455, A+G/C+T 0.800–1.160, spec. rot. +30°–+46.8°.

2. A pharmaceutical composition comprising:
an oligodeoxyribonucleotide having the following analytical parameters: mol. wt. 4000–10000, h<10, A+T/

C+G 1.100–1.455, A+G/C+T 0.800–1.160, spec. rot. +30°–+46.8°; and a pharmaceutically acceptable carrier or excipient.

3. The pharmaceutical composition according to claim 2, wherein said oligodeoxyribonucleotide is present in an amount of from 40 to 160 mg/ml.

4. The pharmaceutical composition according to claim 2, wherein said oligodeoxyribonucleotide is present in an amount of from 80 to 160 mg/ml.

5. The pharmaceutical composition according to claim 2, wherein said oligodeoxyribonucleotide is present in an amount of from 200 to 1500 mg/ml.

6. An oligodeoxyribonucleotide as recited in claim 1, wherein said spec. rot. is in the range of from +30°–+46.2°.

7. A composition as recited in claim 2, wherein said spec. rot. is in the range of from +30°–+46.2°.

* * * * *